US 10,537,550 B2
Jan. 21, 2020

(54) METHODS OF TREATING UNDERLYING INFLAMMATION FROM COPD OR ASTHMA

(75) Inventors: Joachim Goede, Hanau (DE); Joachim Maus, Mülheim (DE); Peter Jürgen Cnota, Bad Homburg (DE); Istvan Szelenyi, Schwaig (DE)

(73) Assignee: MEDA PHARMA GMBH & CO. KG (DE)

( * ) Notice: Subject to any disclaimer, the term of this patent is extended or adjusted under 35 U.S.C. 154(b) by 0 days.

(21) Appl. No.: 12/189,598

(22) Filed: Aug. 11, 2008

(65) Prior Publication Data

US 2008/0300226 A1    Dec. 4, 2008

Related U.S. Application Data

(63) Continuation of application No. 11/051,468, filed on Feb. 7, 2005, now abandoned.

(60) Provisional application No. 60/541,956, filed on Feb. 6, 2004.

(51) Int. Cl.
*A61K 31/401* (2006.01)
*A61K 31/4015* (2006.01)
*A61K 31/573* (2006.01)

(52) U.S. Cl.
CPC .................................. *A61K 31/401* (2013.01)

(58) Field of Classification Search
CPC . A61K 31/401; A61K 31/4015; A61K 31/573
See application file for complete search history.

(56) References Cited

U.S. PATENT DOCUMENTS

| | | | |
|---|---|---|---|
| 5,712,298 | A | 1/1998 | Amschler et al. |
| 6,086,914 | A | 7/2000 | Weinstein et al. |
| 6,204,285 | B1 * | 3/2001 | Fabiano et al. ............... 514/424 |
| 6,384,038 | B1 | 5/2002 | Rubin |
| 6,402,285 | B1 | 6/2002 | Endo et al. |
| 6,475,467 | B1 | 11/2002 | Keller et al. |
| 6,645,466 | B1 | 11/2003 | Keller et al. |
| 7,258,118 | B2 | 8/2007 | Goede et al. |
| 7,985,766 | B2 | 7/2011 | Goede et al. |
| 8,048,910 | B2 | 11/2011 | Maus et al. |
| 8,518,918 | B2 | 8/2013 | Maus et al. |
| 2001/0025040 | A1 | 9/2001 | Poppe et al. |
| 2001/0027789 | A1 | 10/2001 | Goede et al. |
| 2002/0115681 | A1 | 8/2002 | Bozung et al. |
| 2002/0151597 | A1 | 10/2002 | Banerjee et al. |
| 2003/0068280 | A1 * | 4/2003 | Bannister et al. ............... 424/46 |
| 2003/0109510 | A1 | 6/2003 | Gavin |
| 2003/0119802 | A1 * | 6/2003 | Gavin ........................... 514/179 |
| 2004/0002548 | A1 | 1/2004 | Bozung et al. |
| 2004/0028734 | A1 | 2/2004 | Bannister et al. |
| 2004/0038958 | A1 | 2/2004 | Rundfeldt et al. |
| 2004/0053902 | A1 | 3/2004 | Smith |
| 2005/0288265 | A1 | 12/2005 | Locher et al. |
| 2006/0081246 | A1 | 4/2006 | Goede et al. |
| 2006/0147382 | A1 | 7/2006 | Bundschuh et al. |

FOREIGN PATENT DOCUMENTS

| | | | |
|---|---|---|---|
| EP | 1449528 | 8/2004 | |
| WO | WO-01/76575 | 10/2001 | |
| WO | WO-02/069945 | 9/2002 | |
| WO | WO-02078671 | 10/2002 | |
| WO | WO-02/096423 | 12/2002 | |
| WO | WO-02/096463 | 12/2002 | |
| WO | WO-03/011274 | 2/2003 | |
| WO | WO-2004019984 | 3/2004 | |
| WO | WO-2004/084897 | 10/2004 | |
| WO | WO 2005/05999 A1 * | 6/2005 | ........... A61K 31/216 |

OTHER PUBLICATIONS

Austen et al at p. 856 (Austen et al. Samter's Immunologic Diseases. Philadelphia: Lippincott Williams & Wilkins, 2001.*
Brostoff et al. Clinical Immunology. London: Gower Medical Publishing, 1991.*
Gennaro, Alfonso. Remington's: Pharmacetical Sciences. Easton, PA:Mack Publishing Co., 1985.*
Roitt et al. Immunology. 3rd Ed. St. Louis: Mosby, 1993.*
Rogers et al. (The Journal of Neuroscience. Apr. 11, 2012; 32(15):5237-5241).*
The Free Dictionary. "Dosage" (TheFreeDictionary.com/dosage. Accessed Dec. 24, 2013.).*
Gupta et al., Postgrad. Med. J., vol. 81, pp. 236-242 (2005).*
Ohri et al. (BMC Cancer 2010, 10:323).*
Johnson et al., British Journal of Cancer, vol. 84(10), pp. 1424-1431 (2001).*
Gura (Science, vol. 278, pp. 1041-1042 (1997)).*
Barnes (Pharmacol Rev. vol. 56 (4):515-548. 2004).*
Elborn et al. (Pediatric Pulmonology. vol. 19, Issue 4, Oct. 2005).*
Lotvall, Jan. Advances in Combination Therapy for Asthma and COPD. West Sussex, UK: John Wiley & Sons, Ltd., 2012. pp. 320-321.*
Murugan et al., "Signal transduction pathways linking the activation of alveolar macrophages with the recruitment of neutrophils to lungs in chronic obstructive pulmonary disease." Exp Lung Res. Aug. 2009;35(6):439-85.*
Peter Barnes, D.Sc., F.R.C.P. ("Unexpected Failure of Anti-Tumor Necrosis Factor Therapy in Chronic Obstructive Pulmonary Disease". American Journal of Respiratory and Critical Care Medicine. vol. 175, No. 9:866-867. May 1, 2007).*
Vaart et al. ("First Study of Infliximab Treatment in Patients with Chronic Obstructive Pulmonary Disease". American Journal of Respiratory and Critical Care Medicine. vol. 172, No. 4:465-469. Aug. 15, 2005.*

(Continued)

*Primary Examiner* — Rachael E Bredefeld
*Assistant Examiner* — Chris E Simmons

(57) ABSTRACT

The present invention describes the combination of topically inhaled medicinal formulations comprising an anticholinergic component and a glucocorticosteroid component and its use in the symptomatic and prophylactic treatment of diseases of the respiratory tract, especially with an obstructive component or underlying inflammation like asthma and chronic obstructive pulmonary disease (COPD). It further comprises the presentation of this combination in a locally applied (inhaled) formulation and application in an inhalation device for instance in the NOVOLIZER®.

14 Claims, No Drawings

(56) References Cited

OTHER PUBLICATIONS

Jason Adamson, Linsey E Haswell, Gary Phillips and Marianna D Gaga (2011). In Vitro Models of Chronic Obstructive Pulmonary Disease (COPD), Bronchitis, Dr. Ignacio MartÁ-n-Loeches (Ed.), InTech, DOI: 10.5772/18247. Available from: https://www.intechopen.com/books/bronchitis/in-vitro-models-of-chronic-obstructive-pulmonary-disease-copd.*

Tzelepis ("Comparison of nebulized glycopyrrolate and metaproterenol in chronic obstructive pulmonary disease." Eur Respir J, 1996, 9, 100-103). (Year: 1996).*

Szafranski ("Efficacy and safety of budesonide/formoterol in the management of chronic obstructive pulmonary disease". Eur Respir J 2003; 21: 74-81). (Year: 2003).*

Pahl, Andreas, Possible Synergistic Effects f R,S/S,R-glycopyrolate and Tiotropium with the Glucocorticoid Budesonide, Viatris; No. 2006-03, Jul. 19, 2006.

Herbst et al., "Selective oral epidermal growth factor receptor tyrosine Kinase inhibitor zD1839 is generally well-tolerated and has activity in non-small-cell lung cancer and other solid tumors: results of a Phase I trial" Journal of Clinical Oncology, Sep. 15, 2002, vol. 20, No. 18, pp. 3815-3825.

Mueller et al., "Development of a powder for inhalation with R,R-glycopyrrolate as active ingredient for the delivery from novel multidose dry powder inhaler" European Respiratory Society Annual Congress 2003, Sep. 27, 2003, abstract 2977.

Finsnes et al., "Leukotriene antogonism reduces the generation of endothelin-I and interferon-gamma and inhibits eosinophili airway inflammation" Respiratory Medicine, 2002, vol. 96, pp. 901-906.

Reid P., "Roflumilast", Current Opinion in Investigational Drugs, Current Drugs, London, GB, vol. 3, No. 8, Aug. 2002, pp. 1165-1170, XP001119630, ISSN: 0967-8298 Abstract.

Santing et al., "Phosphodiesterase inhibitors reduce bronchial hyper-reactivity and airway inflammation in unrestrained guinea pigs", European Journal of Pharmacology, vol. 275, No. 1, pp. 75-82 (Feb. 4, 1992).

International Search Report dated Nov. 23, 2005, issued in PCT/EP2005/000649.

* cited by examiner

METHODS OF TREATING UNDERLYING INFLAMMATION FROM COPD OR ASTHMA

CROSS-REFERENCE TO RELATED APPLICATIONS

This application is a continuation of U.S. patent application Ser. No. 11/051,468, filed Feb. 7, 2005, now abandoned, which claims priority to U.S. Provisional Application No. 60/541,956, filed Feb. 6, 2004, the subject matter of both being incorporated herein by reference.

The present invention describes the combination of topically inhaled medicinal formulations comprising an anticholinergic component and a glucocorticosteroid component and its use in the symptomatic and prophylactic treatment of diseases of the respiratory tract, especially with an obstructive component or underlying inflammation like asthma and chronic obstructive pulmonary disease (COPD). It further comprises the presentation of this combination in a locally applied (inhaled) formulation and application in an inhalation device for instance in the NOVOLIZER®, a breath-activated, multidose, refillable pressurized metered dose inhaler.

One of the most important diseases of the respiratory tract are obstructive airway diseases like COPD or asthma. The prevalence of COPD increases heavily with age. The Global Burden of Disease study, undertaken by the World Bank and World Health Organization, concluded that COPD worldwide will increase from 1990 to 2020 its rank number of death from rank 6 to rank 3, and its rank number of disability-adjusted life years lost from rank 12 to rank 5 (Gulsvik, Monaldi Arch Chest Dis. 2001 June; 56(3):261-4). Chronic obstructive pulmonary disease (COPD) is increasing worldwide and affects nearly 16 million Americans, and more than $18 billion is spent annually on medications, physician visits, and hospitalizations. COPD is characterized by chronic airflow obstruction with episodic acute exacerbations, which result in increased morbidity and mortality. Patients hospitalized with exacerbations have an overall mortality rate of 3% to 4%, and up to 24% of patients requiring care in the intensive care unit die (Blanchard, Clin Cornerstone. 2003; 5(1):28-36). Bronchial asthma remains a significant cause of mortality at all ages as well (Sidebotham und Roche, Histopathology. 2003 August; 43(2):105-17).

Bronchial asthma causes characteristic histological changes in the mucosa of the airways which includes fibrous thickening of the lamina reticularis of the epithelial basement membrane, smooth muscle hypertrophy and hyperplasia, increased mucosal vascularity and an eosinophil-rich inflammatory cell infiltrate (Sidebotham and Roche, Histopathology. 2003 August; 43(2):105-17). In COPD, chronic inflammation leads to (partially) fixed narrowing of small airways and alveolar wall destruction (emphysema) (Barnes, Annu Rev Med. 2003; 54:113-29. Epub 2001 Dec. 3). Thus, both diseases comprise a kind of narrowing of the small airways due to smooth muscle hypertrophy and a kind of inflammatory process as well. The management of the diseases consists therefor on the one hand of a symptomatic reliever medication which dilates the small airways and on the other hand of a causal treatment which controls the underlying inflammation process. Inhaled anticholinergic agents (and ß2-adrenoreceptor agonists) are the mainstay in the symptomatic bronchodilating treatment of COPD (GOLD Guideline, 2002) and asthma (GINA Guideline, 2002). And inhaled glucocorticosteroids are the most effective preventer (=controller) medication (Van Asperen, Med J. Aust. 2002 Sep. 16; 177 Suppl:S64-6). However, a causal treatment with anticholinergic agents is not possible, nor a rapid symptomatic relief is expected with glucocorticosteroids.

Anticholinergic agents are exemplified by the belladonna alkaloids atropine and scopolamine, which inhibit the muscarinic action of acetylcholine on structure innervated by postganglionic cholinergic nerves. These agents typically inhibit bronchoconstriction by relaxing of smooth muscles and cause considerable bronchodilation. Anticholinergic agents also are known to exert central effects which include pupil dilatation and stimulation and/or depression of the central nervous system. Novel anticholinergic pharmaceuticals have been developed which have a limited capacity to pass across the blood-brain barrier, and therefore have a limited capacity to produce central effects. Examples of these agents are the quaternary ammonium compounds methscopolamine, ipratropium, tiotropium and the enantiomers of glycopyrrolate.

Antimuscarinic treatment of asthma and COPD has a relatively long history leading to its present day use as an effective bronchodilating drug for obstructive pulmonary diseases. Present formulations are, however, limited to oxitropium, ipratropium, and the recently approved tiotropium bromide.

Anticholinergics are agents of first choice for the symptomatic treatment of patients with COPD. In acute exacerbation of chronic obstructive pulmonary disease, inhaled bronchodilators such as ipratropium bromide have proven useful (Hall et al.). Tiotropium is a long-acting inhaled anticholinergic designed for once-daily bronchodilator treatment of COPD. Tiotropium is a selective antagonist of pulmonary M1 and M3 muscarinic receptor subtypes, that produces a long-lasting (24 hours), dose-dependent bronchodilation and bronchoprotection against constrictive stimuli, e.g. methacholine, following inhalation of single doses. Clinical trials with tiotropium in COPD patients over a maximum treatment duration of one year have confirmed a persisting bronchodilator effect of tiotropium compared with placebo and ipratropium, as well as meaningful clinical improvements in lung function, hyperinflation, exercise tolerance, symptom control and quality of life. Moreover, recent trials indicate that treatment with tiotropium also reduces the frequency of COPD exacerbations and hospitalizations. Comparative trials further suggest that the bronchodilator potency of tiotropium may be superior to those of available COPD treatments. Besides a higher incidence of dry mouth, the side effect profile was comparable to ipratropium bromide.

In conclusion, present clinical data suggest that tiotropium has the potential of a first-line treatment for patients with COPD (Beeh et al., Pneumologie. 2003 September; 57(9):519-25). The drug has been shown to improve spirometric parameters, quality of life, and utilization of health care resources (Faulkner et al., Pharmacotherapy. 2003 October; 23(10):1300-15).

Anticholinergic drugs have long since been used in the treatment of chronic obstructive pulmonary disease (COPD) and asthma (Joos, Monaldi Arch Chest Dis. 2000 October; 55(5):411-4). Clinical studies with inhaled tiotropium bromide confirm that it is a potent and long-lasting bronchodilator in COPD and asthma (Barnes et al., Life Sci. 1995; 56(11-12):853-9). Current therapeutic options for acute severe asthma consist of ipratropium and glucocorticosteroids in combination with beta2 selective drugs (McFadden, Am J Respir Crit. Care Med. 2003 Oct. 1; 168(7):740-59). According to the latest evidence, the goals of treatment of adult asthma may be summarized as relief of airflow obstruction by administration of inhaled beta-agonists and anticholinergics, and reduction of airway inflammation and prevention of future relapses by using early administration of s corticosteroids (Rodrigo, Curr Opin Allergy Clin Immunol. 2003 June; 3(3):169-75).

Inhaled glucocorticosteroids are the most effective therapy in controlling chronic asthma symptoms (Barnes, J Aerosol Med. 1996 Spring; 9(1):131-41). Randomized, controlled clinical studies confirm the efficacy of early intervention with inhaled glucocorticosteroids in patients with mild persistent asthma. Regular use of an inhaled glucocorticosteroids can reduce the number of exacerbations and hospitalizations in patients of all ages and with all disease severities (Chapman, Clin Ther. 2003; 25 Suppl C:C2-C14). Within inhaled glucocorticosteroids, fluticasone is endowed of a potent antiinflammatory activity, due to its high affinity for the glucocorticoid receptor (allowing the use of 50% of the dose of other ICS) and of a negligible oral bioavailability (<1%), indicating a low potential for systemic exposure. Due to its high therapeutic index, fluticasone can be used in the management of severe asthma or other airway diseases at doses devoid of relevant unwanted systemic effects. Scientific literature has broadly demonstrated its efficacy and safety, even at high doses and in the long term use (Solidoro et al., Minerva Pediatr. 2003 August; 55(4):345-55). When combined with delivery devices suitable for a spectrum of patient groups, the physical and pharmacokinetic properties of budesonide lend it many of the characteristics of an ideal inhaled glucocorticosteroid, including favorable efficacy and tolerability profiles (O'Connell, Clin Ther. 2003; 25 Suppl C:C4260). Whereas budesonide has clinical efficacy similar to that of other currently available ICSs, it has a good safety profile—and hence a favorable therapeutic margin—that is supported by long-term clinical data (Skoner, Clin Ther. 2003; 25 Suppl C:C61-74).

The practice of using inhaled steroids (ICS) in chronic obstructive pulmonary disease (COPD) is common but controversial (O'Riordan, J Aerosol Med. 2003 Spring; 16(1):1-8). Glucocorticosteroids are probably scarcely effective in COPD patients without overlapping concomitant asthma (Caramori et al., Pulm Pharmacol Ther. 2003; 16(5): 247-77). The routine prescription of these agents to asymptomatic patients with well-preserved lung function is not indicated. However, more selective use of inhaled glucocorticosteroids in patients with moderately severe disease (FEV1<50% predicted) may produce clinical benefit as measured by an increase in FEV1, reduced symptoms and fewer exacerbations (O'Riordan, J Aerosol Med. 2003 Spring; 16(1):1-8). Glucocorticosteroids should mainly be used to reduce exacerbations and improve the health status of these patients (Man et al., JAMA. 2003 Nov. 5; 290(17): 2313-6). But it has to be admitted that current pharmacological treatment of COPD is unsatisfactory, as it does not significantly influence the severity of the disease or its natural course.

As the current treatment of asthma and COPD is not satisfactory improved, the problem underlying the present invention was to provide effective and more convenient therapeutic interventions.

A solution is given by the combination of inhaled glycopyrrolate with an inhaled glucocorticoid like budesonide, fluticasone, ciclesonide, or beclometason.

Glycopyrrolate belongs to the so-called quaternary ammonium anticholinergic drugs and antagonizes the neurotransmitter acetylcholine at its muscarinic receptors. This effect leads to a considerable smooth muscle relaxation resulting in a prolonged bronchodilating effect. Due to the fast onset and the long duration of action anticholinergic agents are the first choice for the symptomatic treatment of COPD.

Topically inhaled glucocorticosteroids such as budesonide and fluticasone suppress inflammation in asthmatic airways by affecting the transcription of several steroid-responsive genes and have become first-line therapy for the long-term asthma control.

Surprisingly, the combination of a symptomatic and a causal treatment is superior to that of the mono-compounds resulting in over-additive effects and/or diminished side-effects, respectively. Therefore, the combination can be useful in the treatment of obstructive airway diseases of different origins like COPD or asthma.

Surprisingly it has been revealed that the use of topically inhaled anticholinergic agents such as glycopyrrolate, including one of its enantiomers, especially R,R-glycopyrrolate or their physiologically acceptable salts or a mixture thereof administered in combination with topically inhaled glucocorticosteroids is effective and safe in the treatment of asthma and chronic obstructive pulmonary disease (COPD) which allows for lower doses or which decreases side-effects.

Consequently, the combination of such drugs leads to a better efficacy which is surprisingly overadditive and an improved tolerability with less side-effects than expected.

EXPERIMENTAL PART

The influence of R,R-glycopyrrolate in combination with glucocorticoids on TNFα release was investigated by using human peripheral blood mononuclear cells (PBMCs). The study was approved by our institutional Ethics Committee according to the International Declarations of Helsinki and Tokyo.

PBMCs were isolated from heparinized blood samples of healthy donors by density gradient centrifugation. An equal volume of Hanks buffer (Life Technologies, Heidelberg, Germany) is added to heparinized whole blood samples. 15 ml Histopaque-1077 (Sigma, Deisenhofen, Germany) are overlayed with a maximum of 40 ml of blood/Hanks mixture were centrifuged for 30 min at room temperature (2000 rpm). A visible band containing PBMCs is transferred to a fresh tube and washed twice with Hanks-buffer. Finally cells are seeded in RPMI 1640 Medium (Life Technologies, Heidelberg, Germany) with Glutamax I (Gibco BRL, Eggenstein) and 10% FCS (Boehringer Mannheim, Penzberg, Germany). After isolated, PBMCs were cultured in RPMI 1640 medium supplemented with 10% fetal calf serum (FCS) at 37° C. 5% $CO_2$ overnight. Monocytes were isolated from other cells by adherence method, non-adherent cells were removed by changing the medium.

Cells are re-suspended at 106 cells/ml and incubated in 500 μl volumes in 24-well tissue culture plates (Falcon Becton Dickinson Labware) at 37° C., 5% $CO_2$. After pre-incubation with test substances (0.5 μl/500 μl medium) for 30 min, cells were stimulated with lipopolysaccharide (LPS) (1 μg/ml). At indicated times cells were sedimented by centrifugation, the supernatants were harvested and kept frozen at −80° C. until protein determination; the cells were lysed by RLT lysis Buffer (Qiagen, Hilden, Germany) and frozen at −80° C. until analysis.

Cytokine measurements in culture supernatants are done by sandwich ELISA using matched antibody pairs (Pharmingen, Heidelberg, Germany). ELISA plates (Maxisorb, Nunc) are coated overnight with anti-cytokine monoclonal antibody (mAb) in 0.1 M carbonate buffer, pH 9.5. After being washed, plates are blocked with Assay Diluent (Pharmingen, Heidelberg, Germany) for 1 h and washed again. Appropriately diluted supernatant samples and standards are distributed in duplicates and the plates are incubated for 2 h at room temperature. Plates are washed, incubated for 1 h with working detector (biotinylated anti-cytokine antibody and Avidin-horseradish peroxidase conjugate). After washing, substrate (TMB and hydrogen peroxide) is added. The reaction is stopped by adding of 1M $H_3PO_4$. Plates are read at 450 nm (reference 570 nm) in a microplate reader (Dynatech). The results are expressed as a percentage of the control level of cytokines production by cells stimulated in the absence of the compound.

Upon LPS-stimulation, basal TNFα release from monocytes increased from 328 pg/ml up to 7,258 pg/ml. R,R-glycopyrrolate alone did not influence the LPS-induced TNFα release up to 10 μmol/l. The glucocorticoid budesonide inhibited the TNFα release in a concentration-dependent manner. The $IC_{50}$ value of budesonide amounted to 0.55±0.13 nmol/l. The simultaneous addition of 10 μmol/l of R,R-glycopyrrolate surprisingly and highly significantly reduced the $IC_{50}$ to 0.13±0.03 nM (p=0.0251).

The data show that R,R-glycopyrrolate significantly enhances the anti-inflammatory activity of glucocorticoids with increased efficacy which is surprisingly overadditive and a better tolerability with reduced occurrence of side-effects than at administration of the monocompounds.

The combination therapy disclosed by this invention comprises administering a glucocorticosteroid together with a long-acting anticholinergic bronchodilator to prevent onset of a pulmonary disease event or to treat an existing condition and to reduce obstruction and airway inflammation.

The compounds may be administered together in a single dosage form. Or they may be administered in different dosage forms. These drugs are usually administered as an aerosol (with or without propellant), or as an inhaled powder for instance with the NOVOLIZER®. This invention contemplates either co-administering both drugs in one delivery form such as an inhaler, that is putting both drugs in the same inhaler. Formulations are within the skill of the art and may contain all usual excipients, adjuncts, and additives.

The active ingredients may be given from 1 to 8 times a day, sufficient to exhibit the desired activity. Preferably, the active components are given about once or four times a day, more preferably once or twice a day. The compounds of the combination may be administered at the same time. Or they may be administered either close in time or remotely, such as where one drug is administered in the morning and the second drug is administered in the evening. Or in another scenario, one drug could be taken twice daily and the other once daily, either at the same time as one of the twice-a-day dosing occurred, or separately. Preferably both drugs should be taken together at the same time.

The inhaled anticholinergic drug, racemic glycopyrrolate, one of its enantiomers, especially R,R-glycopyrrolate or a mixture thereof and its salts, solvates and hydrates can be administered in an amount of between 5 and 500 μg/day adult human with the preference of 15 to 300 μg/day in dependence of the magnitude of symptoms. A dosage range between 5 and 100 μg/day is especially preferred.

Glucocorticosteroids (budesonide or ciclesonide or fluticasone or mometasone or flunisolide, or beclometason or loteprednol) can be administered inhaled in conformity with approved labeling in an amount of 100 to 1.600 μg/day preferably between 200 and 400 μg/day.

The combination may be used prophylactically or after the onset of symptoms has occurred. In some instances the combination(s) may be used to prevent the progression of a pulmonary disease or to arrest the decline of a function such as lung function.

The following examples describe the invention without limiting it.

Example 1

Powder Inhalation with 250 μg Fluticasone and 20 μg Glycopyrrolate Per Single Dose A quantity of 250 g micronized fluticasone is mixed with 1000 g alpha lactose monohydrate, the mixture is given on a sieve of 0.5 mm mesh size and finally mixed again. 20 g micronized glycopyrrolate is mixed with 100 g alpha lactose monohydrate, the mixture is given on a sieve of 0.8 mm mesh size and finally mixed again. The two mixtures received are blended and filled up with alpha lactose monohydrate to 15000 g. Subsequently, it is mixed again and the powder mixture received is filled in powder inhalers releasing 15 mg of powder per single dose. Per single dose, 250 μg fluticasone and 20 μg glycopyrrolate are released from a powder inhaler and supplied to the patient's airways.

Example 2

Dosage Aerosol with 100 μg Fluticasone and 10 μg Glycopyrrolate Per Single Dose

A quantity of 1000 g 1,1,1,2,3,3,3 heptafluoropropane (=HFA 227) is cooled down at a temperature of −55° C. and, while stirring, mixed with a solution of 11.7 g polyoxethylene-25-glyceryl-trioleate (trade name: Tagat TO) in 11.7 g absolute ethanol. Subsequently, 1500 mg micronized fluticasone and 150 mg micronized glycopyrrolate is added, and the suspension produced is intensively homogenized. While further cooling and stirring, the suspension is filled up with refrigerated propellant 227 to 1170 g and after mixing again filled in metal cans which are closed with metering valves releasing 50 μl of the suspension per actuation. Thus, 100 μg fluticasone and 10 μg glycopyrrolate are released per actuation.

The invention claimed is:

1. A method of treating underlying inflammation caused by chronic obstructive pulmonary disease (COPD) or asthma in a mammal, comprising:
   administering an effective amount of a pharmaceutical composition comprising synergistically effective amounts of R,R-glycopyrrolate and budesonide, or physiologically acceptable salts thereof, to said mammal,
   wherein treating inflammation caused by COPD or asthma results in an inhibition of TNFα release from a peripheral blood mononuclear cell (PBMC) of said mammal,
   wherein the inhibition of TNFα release from the PBMC of said mammal caused by the administration of the pharmaceutical composition is greater than inhibition of TNFα release from a PBMC of said mammal caused by administration of R,R-glycopyrrolate or budesonide alone, as measured by enzyme-linked immunosorbent assay (ELISA).

2. The method of claim 1, wherein the pharmaceutical composition comprising R,R-glycopyrrolate and budesonide is administered in a single dosage form.

3. The method of claim 1, wherein the mammal is a human.

4. The method according to claim 1 wherein the mammal is selected from the group consisting of cats, dogs, and horses.

5. The method according to claim 1 wherein an adult human is treated with a daily dosage of R,R-glycopyrrolate of 5 to 500 μg/day and a daily dosage of budesonide of 100 to 1,600 μg/day.

6. The method of claim 5 wherein the daily dosage of R,R-glycopyrrolate is 15 to 300 μg/day.

7. The method of claim 5 wherein the daily dosage of budesonide is 200 to 400 μg/day.

8. The method according to claim 1 wherein an adult human is treated with a daily dosage of R,R-glycopyrrolate of 5 to 100 μg/day and a daily dosage of budesonide of 100 to 1,600 μg/day.

9. The method of claim 8 wherein the daily dosage of budesonide is 200 to 400 μg/day.

10. The method of claim 1, wherein the pharmaceutical composition comprising R,R-glycopyrrolate and budesonide is administered by inhalation.

11. The method of claim 10, wherein the pharmaceutical composition comprising R,R-glycopyrrolate and budesonide is administered as an aerosol.

12. The method of claim 10, wherein the pharmaceutical composition comprising R,R-glycopyrrolate and budesonide is administered as a powder.

13. A method of inhibiting TNFα release from an isolated peripheral blood mononuclear cell (PBMC), comprising:
   administering an effective amount of a pharmaceutical composition comprising synergistically effective amounts of R,R-glycopyrrolate and budesonide, or physiologically acceptable salts thereof, to the isolated PBMC, and
   inhibiting TNFα release from the isolated PBMC, wherein the inhibition of TNFα release by the administration of the pharmaceutical composition is greater than inhibition of TNFα release by administration of R,R-glycopyrrolate or budesonide alone.

14. The method of claim 3, wherein the R,R-glycopyrrolate and budesonide are administered once-daily.

\* \* \* \* \*